United States Patent [19]
Roth

[11] 3,939,821
[45] Feb. 24, 1976

[54] MAGNETICALLY ACTUATED TUBE COMPRESSING VALVE

[75] Inventor: Russell B. Roth, Erie, Pa.

[73] Assignee: Altair, Incorporated, Plymouth, Conn.

[22] Filed: Feb. 25, 1975

[21] Appl. No.: 552,935

Related U.S. Application Data

[63] Continuation of Ser. No. 415,645, Nov. 14, 1973, abandoned.

[52] U.S. Cl................ 128/1 R; 128/285; 128/346; 128/DIG. 25
[51] Int. Cl.²........................................ A61B 19/00
[58] Field of Search............ 128/1 R, 1.4, 1.3, 274, 128/270, 285, 349, 346, DIG. 25; 251/65

[56] References Cited
UNITED STATES PATENTS

| | | | |
|---|---|---|---|
| 2,638,093 | 5/1953 | Kulick | 128/DIG. 25 |
| 3,419,008 | 12/1968 | Plishner | 128/346 |
| 3,565,073 | 2/1971 | Giesy | 128/283 |
| 3,687,129 | 8/1972 | Nuwayser | 128/1 R |
| 3,731,670 | 5/1973 | Loe | 128/1 R |
| 3,750,194 | 8/1973 | Summers | 128/1 R X |

*Primary Examiner*—Dalton L. Truluck
*Attorney, Agent, or Firm*—Littlepage, Quaintance, Murphy & Dobyns

[57] ABSTRACT

A valve for compressing a duct or vessel within a living animal having a permanent magnetic core enveloped by a biochemically inert sheath surgically implanted adjacent the duct or vessel and actuated by a magnet topically positioned by a belt, adhesive patch or other means.

14 Claims, 5 Drawing Figures

MAGNETICALLY ACTUATED TUBE COMPRESSING VALVE

This is a continuation of application Ser. No. 415,645, filed Nov. 14, 1973, now abandoned.

BACKGROUND OF THE INVENTION

1. Field of the Invention

This invention relates to tube compressing valves having a permanent magnet actuator and particularly relates to such a valve which may be advantageously used within an animal's body to extracorporeally control fluid flow.

2. Description of Prior Art

Within the body of animals and particularly humans are many liquid-carrying tubes or ducts subject to voluntary or involuntary control by the body. Such control is often lost due to spinal cord or brain injury, disease, accidental or surgical damage, congenital defect, or other similar cause. It is then desirable that such control be re-established by artificial means which would cause the least disruption to the system involved as well as other tissues in the body. It is also occasionally desirable to establish an external or extracorporeal control to experimentally examine abnormal bodily functions or periodically prevent the fluid flow in particularly important time frames.

Previous means for controlling the liquid flow through tubes of ducts within the body have often required placing an element within the duct or tube, thus subjecting that element to possibily detrimental chemical action. With the element so placed, the liquid flow is never returned to normal due to the constriction presented by the element even when fully opened.

Other efforts to establish control over fluid transport have involved surgical procedures for a rearrangement of muscles and fascias with or without the implantation of bone segments or inert foreign bodies for the purpose of appropriate compression of the tubes.

Still other means have been suggested requiring major surgery, which establishes control by the fluid pressure exerted by silicone filled elements placed adjacent the duct with control straps or tubes extending, often over a considerable distance, to an accessible control point. Considerable postoperative treatment is generally required and the results are not always as satisfactory as one might reasonably wish.

Previous means having moving elements face the additional problem of being susceptable to tissue infusion over a period of time, thereby preventing the relative movement necessary for correct operation and ultimately resulting in failure of the control means.

Examples of prior art are to be found in U.S. Pat. Nos. 3,731,670; 3,642,004; 3,419,008; 2,921,584 and 2,455,859.

SUMMARY OF THE INVENTION

A first permanent magnet is enclosed and sealed within a biologically and biochemically inert sheath means. The sheath means which contiguously surrounds the first magnet is adapted to be attached to tissue adjacent the tube or duct to be controlled by suturing or other equivalent methods. The sheath can additionally be adapted for tissue infusion, thereby increasing the positional stability of the first magnet.

The first magnet and contiguous sheath means is surgically implanted in the tissue adjacent the duct sought to be controlled on a side opposite the nearest convenient body surface. A second magnet is selectively positioned extracutaneously to interact with the first magnet causing the first magnet and contiguous sheath means to exert a force on the tube or duct, thereby clamping the duct in such a position as to stop the flow of liquid therethrough.

Appropriate means for positioning the second magnet for insuring magnetic interaction is designed to conform to the demands of the particular application. The means for positioning the second magnet can be an adhesive patch, a strap or belt, or portion thereof for securing the second magnet to a particular position of the body. The positioning means can also include a slim, elongated element having the second magnet at one end thereof for retrievably inserting the second magnet in an appropriate natural body cavity.

The first magnet and contiguous sheath means is not exposed to the actual liquid flow through the duct, but is positioned and secured to tissue adjacent to the duct. This allows the free and unobstructed flow of liquid through the duct in a natural fashion when the valve is not in a clamping position. Further, the first magnet and contiguous sheath means are compact and secured only to adjacent tissue, thus eliminating the need for major surgical procedures.

The second magnet and means for positioning the second magnet can also include a magnetic shielding or pole shading means for preventing the magnetic interaction between the first and second magnet without the necessity of positionally displacing the second magnet.

Other features and advantages will become apparent from the following examples utilizing the invention.

DESCRIPTION OF A PREFERRED EMBODIMENT

Figure 1:
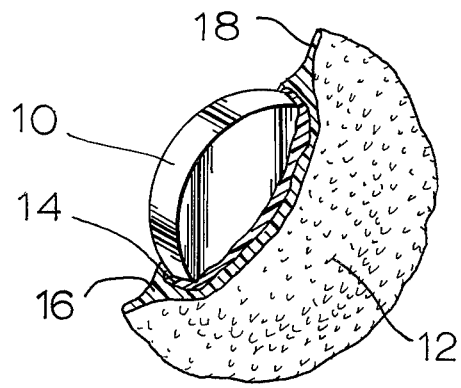
FIG. 1 is a perspective detail of a first permanent magnet and contiguous sheath means.

A first element of a valve according to the invention, shown in FIG. 1, comprises a first permanent magnet 10 enveloped by a contiguous sheath means 12. The magnet preferably has a high field strength. Acceptable materials for the permanent magnet are oriented ferrite, platinumcobalt, and the ALNICO series. The preferred material is the REACO-1 samarium cobalt rare earth permanent magnet material available from Raytheon Company of Waltham, Massachusetts.

The contiguous sheath means can have an inner impermeable core portion 14 immediately adjacent the permanent magnet for preventing the chemical interaction between the permanent magnet 10 and any surrounding environment. The sheath means can also have an outer portion 16 having a radially extending portion 18 for securing the permanent magnet and sheath means to any surrounding tissue by means of sutures or other equivalent means. The outer portion 16 can be porous to allow tissue infusion into the surface from the adjacent tissue areas, thereby increasing the positional stability of the magnet and sheath without preventing the necessary valving action.

Both portions of the contiguous sheath are preferably made of a biochemically inert and non-allergenic organic polymer, such as the halogenated polyolefins, for example, polytetrafluoroethylene. Other similar materials can be used which meet the biochemical requirements and which can withstand the necessary preoperative sterilization.

The second permanent magnet and means for positioning the second magnet are best discussed in conjunction with the examples of use which follow, but generally the choice of materials for the second magnet are the same as for the first magnet. The second magnet is placed extracutaneously adjacent the first implanted magnet to interact therewith for causing a clamping of the desired duct or tube. Although the second magnet may be positioned by appropriate means within natural body cavity, this is to be considered as within the meaning of extracutaneously; that is, on the outside of the continuous natural barrier formed by the skin and natural body cavity walls. This is to be distinguished from the placement of the first magnet which is subcutaneous and within the tissue immediately adjacent the duct over which control is sought.

EXAMPLE I

Figure 2:
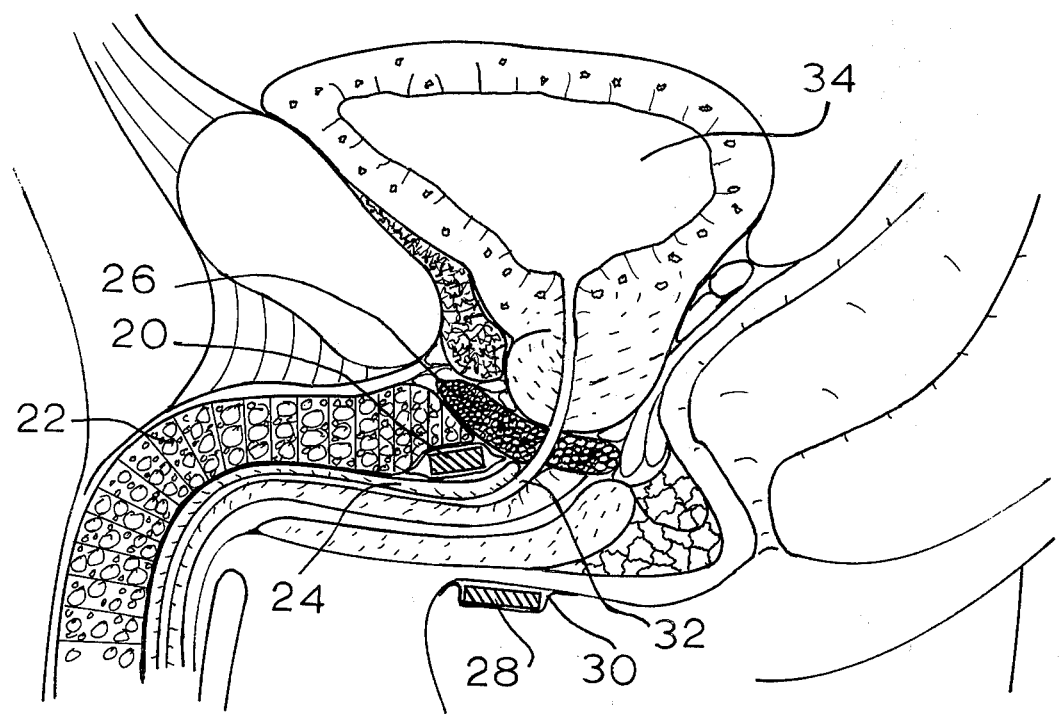
FIG. 2 is a diagrammatic median section of the human male pelvic region.

In the event of incontinence of urination in the human male, it may be desirable to reestablish control of the urethra according to this invention. As shown in FIG. 2, a first magnet and continuous sheath means 20 is surgically implanted between the corpus cavernosum penis 22 and the corpus cavernosum urethae 24, also known as the corpus spongiosum, as close as possible to the urogenital diaphragm 26 and secured to the tunica albuginea membrane or other adjacent tissue.

A second magnet 28 is extracutaneously positioned in the crotch area immediately behind the scrotum by an appropriate positioning means 30 such as a belt or adhesive patch. The interaction between the first and second magnets is such as to pinch the urethra 32 to such an extent as to prohibit the flow or urine from the urinary bladder 34 and yet not cause damage to the cellular makeup of the corpus spongiosum or other tissues. The strength or force of the magnetic interaction is controlled by the choice of size of magnet, the strength of the permanent magnetic field, and the distance between the two magnets.

EXAMPLE II

Figure 3:
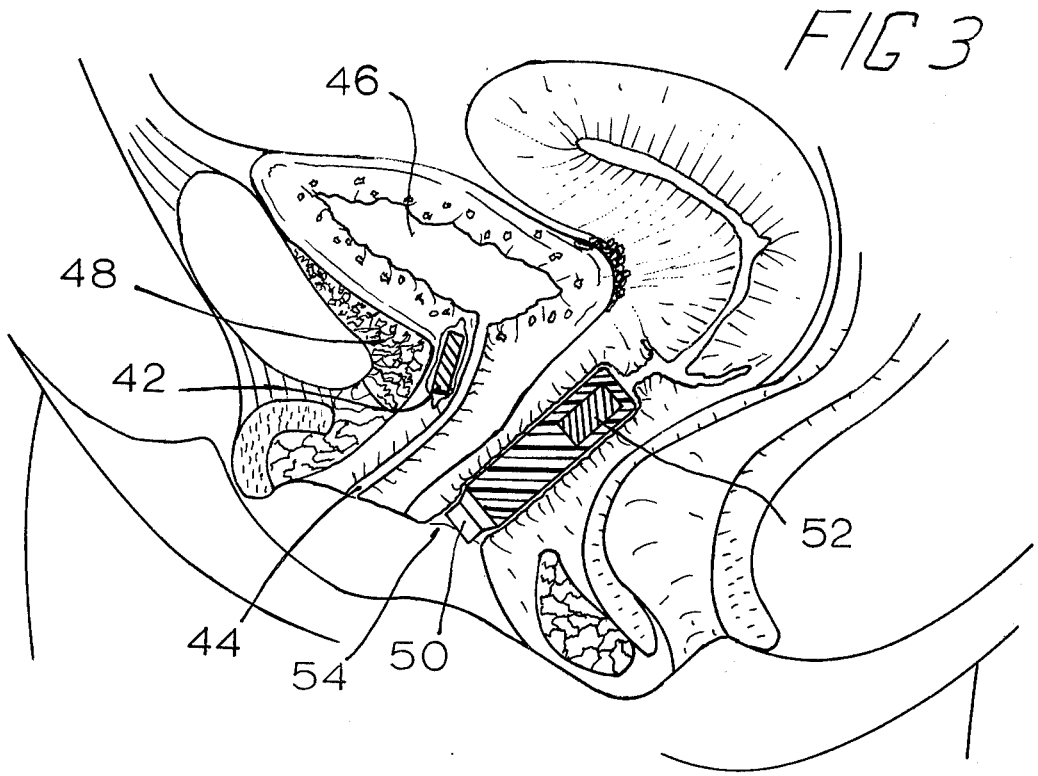
FIG. 3 is a diagrammatic median section of the human female pelvic region.

In the event of incontinence of urination of the human female, due to the dramatic structural differences, a somewhat different solution is necessary. As shown in FIG. 3, a first magnet and sheath means 42 is positioned in front of the urethra 44 as close to the urinary bladder 46 as possible and attached to the areolar tissue, or under the surface of the pubic symphysis in the prevesical space 48.

Figure 4:
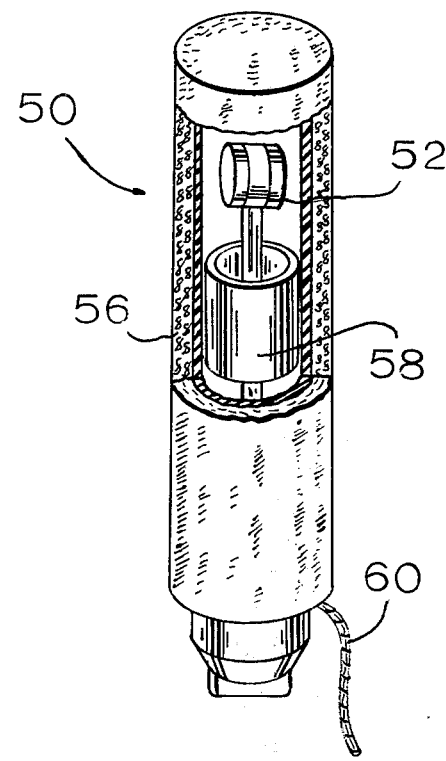
FIG. 4 is a perspective detail of a second magnet and positioning means therefor.

To effect the desired valving action, a slim elongated element 50, as shown in FIG. 4, having a second magnet 52 in one end thereof is inserted in the vaginal cavity 54. The second magnet 52 interacts with the first magnet causing a force on the first magnet in such a way as to clamp the urethra 44 in a position to stop the flow of urine. The positioning means and second magnet fixed therein may be rotated thru 180° to reverse the magnetic polarity of the second magnet, thus applying an opposite force on the first magnet to allow the free and natural flow of liquid through the urethra.

The positioning means can have a removable outer portion 56, for absorbing the natural body emissions during mensuration, thus operating additionally as a conventional tampon.

The means for positioning the second magnet can also have a magnetic shielding means 58 which can be slidably positioned around the second magnet 52 for selectively preventing the magnetic interaction between the first and second magnet, thus allowing urination to occur. A positioning means having a magnetic shielding means removably adjacent the second magnet has the advantage of eliminating any shearing forces on the first magnet, sheath means, and surrounding tissue which would be present if the second magnet were to be slidably removed from the position of magnetic interaction. The removal of the positioning means and second magnet as well as any tampon cap cover or the changing of position of the magnetic shielding or pole shading means may be accomplished with the use of a length of flexible cord 60 appropriately attached.

EXAMPLE III

Figure 5:
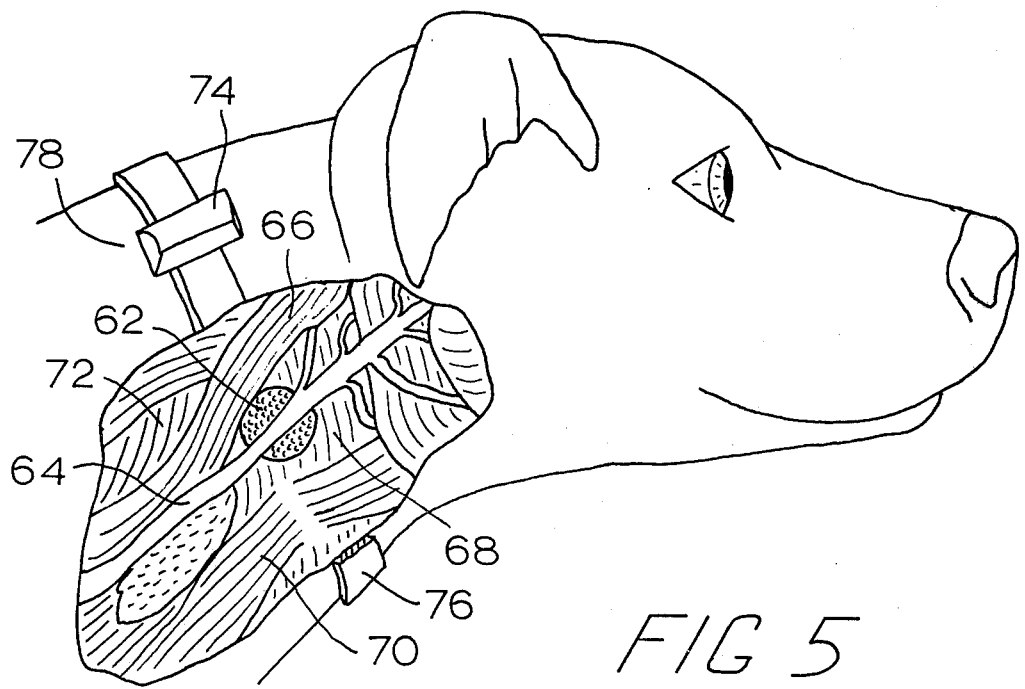
FIG. 5 is a diagrammatic detail of a canine with the carotid artery and adjacent tissues exposed.

It may often become advantageous to constrict or occlude a blood vessel or other similar passageway to conduct studies on abnormally functioning body organs. The occlusion of vessels has proved difficult due to the constant need for adjustment and control, especially in the case of animal specimens. Studies of reduced blood flow due to arteriosclerosis can be simulated by a partial constriction of an artery as shown in FIG. 5.

A first magnet and contiguous sheath means 62 is surgically implanted behind the carotid artery 64 or a branch thereof and attached to the longus colli 66, brachiocephalicus 68, sternocephalicus 70 and/or deep cervical fascia 72 as the particular use may require. A second permanent magnet 74 may be placed within a securely positioned collar 76 to interact with the first magnet. Alternatively, an electromagnet 78, having a magnetic field functionally related to the current therein, can be used to constrict the artery at a predetermined pattern or with a particular designated force. The variables of such a magnetic interaction are well known. The control of the flow of blood through the artery is then simply a function of the current in the electromagnet positioned on the outside of the animal by the positioning means.

Other uses for a valve according to this invention will become apparent to the practitioner from these examples. In all uses it is intended that the first magnet be positionally secured to tissue adjacent to the tube or duct sought to be controlled by means of sutures passing through the periphery of the sheath means contiguously enveloping the first magnet. A second magnet is positioned topically by an appropriate positioning means to effect a pinching or clamping of the duct. Release may be achieved by either moving the second magnet, shielding the second magnet, or otherwise controlling the field of the second magnet.

What is claimed is:

1. A valve means for controlling the flow of liquid through an intercorporeal duct having tissue adjacent thereto comprising a first permanent magnet, a biologically inert sheath means contiguously surrounding the first magnet and immovably fixed with respect to the first magnet for securely attaching the first magnet to said tissue adjacent to said duct, a second magnet, and means for selectively positioning the second magnet extracutaneously adjacent the duct for magnetically interacting with the first magnet thereby causing the first magnet and the sheath means to clamp the duct in a position to stop the flow of liquid therethrough.

2. A valve means according to claim 1 further comprising magnetic shielding means removably adjacent the second magnet for selectively preventing magnetic interaction between the first and second magnet.

3. A valve means according to claim 1 wherein the second magnet is a permanent magnet.

4. A valve means according to claim 1 wherein the second magnet is an electromagnet.

5. A method for selectively preventing the flow of fluid within a duct or vessel of an animal's body comprising the steps of
 implanting a first permanent magnet and contiguous sheath on only one side of the duct or vessel, the sheath being immovably fixed with respect to the permanent magnet,
 securing the sheath to tissue adjacent the duct, and
 topically situating a second magnet so that the magnetic interaction between the first and second magnet provides such a force on the first magnet and sheath as to pinch closed the duct.

6. The method of claim 5 wherein the duct sought to be controlled is the urethra of the human female, and the second magnet is positioned within the vaginal cavity.

7. The method according to claim 5 wherein said duct is located between said first and second magnets and the magnetic interaction between the magnets causing the first magnet and sheath means to clamp the duct is one of attraction.

8. The method according to claim 5 wherein said duct is located on the opposite side of said first magnet from said second magnet and the magnetic interaction between the magnets causing the first magnet and sheath means to clamp the duct is one of repulsion.

9. A valve means adapted to be surgically implanted adjacent to a duct or vessel for selectively controlling the flow of fluid through the duct or vessel, said means comprising a permanent magnet, an inert, impermeable inner sheath enveloping the magnet for preventing any chemical interaction with the magnet and an outer sheath, surrounding the inner sheath and permeable to tissue infusion, for securing the element in a substantially fixed location, the inner sheath and the outer sheath being immovably fixed with respect to the permanent magnet.

10. A valve means for controlling the flow of liquid through an intercorporeal duct having tissue adjacent thereto comprising a first permanent magnet, a biologically inert sheath means contiguously surrounding the first magnet and permeable to tissue infusion for securely attaching the first magnet to said tissue adjacent to said duct, a second magnet, and means for selectively positioning the second magnet extracutaneously adjacent the duct for magnetically interacting with the first magnet thereby causing the first magnet and the sheath means to clamp the duct in a position to stop the flow of liquid therethrough.

11. A valve according to claim 10 wherein the sheath means has an inner impermeable portion immediately adjacent the first magnet and an outer portion permeable to tissue infusion for increasing position stability.

12. A valve means for controlling the flow of liquid through an intercorporeal duct having tissue adjacent thereto comprising a first permanent magnet, a biologically inert sheath means contiguously surrounding the first magnet for securely attaching the first magnet to said tissue adjacent to said duct, a slim, elongated element adapted for insertion in a body cavity and having a removable absorbent outer portion for absorbing body fluids, a second magnet enclosed within one end of said slim, elongated element for insertion within the body cavity adjacent the duct for magnetically interacting with the first magnet, thereby causing the first magnet and the sheath means to clamp the duct in a position to stop the flow of liquid therethrough.

13. A valve means adapted for insertion within a natural body cavity comprising a slim, elongated element, a permanent magnet incorporated within said element and adapted to interact with another subcutaneously placed magnet, and an absorbent, outer portion removably covering said element for absorbing natural body fluids.

14. A valve means for controlling the flow of liquid through an intercorporeal duct having tissue adjacent thereto, comprising a first permanent magnet, a biologically inert sheath means contiguously surrounding the first magnet for securely attaching the first magnet to said tissue adjacent to said duct, a second magnet, magnetically shielding means removably adjacent the second magnet for selectively preventing magnetic direction between the first and second magnet, and means for selectively positioning the second magnet extracutaneously adjacent the duct for magnetically interacting with the first magnet, thereby causing the first magnet and the sheath means to clamp the duct in a position to stop the flow of liquid therethrough.

* * * * *